US006217853B1

(12) United States Patent
Samain et al.

(10) Patent No.: US 6,217,853 B1
(45) Date of Patent: Apr. 17, 2001

(54) USE OF A GUAR GUM IN A PROCESS FOR THE TEMPORARY SHAPING OF KERATIN FIBRES

(75) Inventors: Henri Samain, Bievres; Isabelle Cretois, Clichy, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/425,802

(22) Filed: Apr. 20, 1995

(30) Foreign Application Priority Data

Apr. 25, 1994 (FR) .................................................. 94 04961
Jan. 20, 1995 (FR) .................................................. 95-00658

(51) Int. Cl.[7] ............................... A61K 7/021; A61K 9/00
(52) U.S. Cl. ........................ 424/63; 424/400; 424/70.1; 424/70.13; 424/70.7; 424/78.03
(58) Field of Search ............................ 424/70.13, 70.1, 424/78.03, 70.7, 400, 63

(56) References Cited

U.S. PATENT DOCUMENTS

| | | | |
|---|---|---|---|
| 4,292,212 | * 9/1981 | Melby ................................. | 252/547 |
| 4,472,297 | 9/1984 | Bolich, Jr. et al. .................. | 252/531 |
| 4,847,076 | * 7/1989 | Deshpande ........................ | 424/70.13 |
| 5,047,177 | * 9/1991 | Vanco ................................. | 252/548 |

FOREIGN PATENT DOCUMENTS

| 0018717 | 11/1980 | (EP) . |
|---|---|---|
| 2129455 | * 5/1984 | (GB) . |

OTHER PUBLICATIONS

McCarthy, *Every Woman's Beauty Basics*, p. 164–169 (1994).*

Zviak, *The Science of Hair Care*, p. 153–156 (1986).*

* cited by examiner

*Primary Examiner*—Thurman K. Page
*Assistant Examiner*—Amy E Pulliam
(74) *Attorney, Agent, or Firm*—Finnegan, Henderson, Farabow, Garrett & Dunner L.L.P.

(57) ABSTRACT

A method using at least one guar gum as the sole shape-retention and/or shaping agent in cosmetic compositions intended for a temporary shaping of keratin fibers, and a method for the temporary shaping and/or deformation of keratin fibers, in particular in the shape of a hairsetting, using this compound.

2 Claims, No Drawings

USE OF A GUAR GUM IN A PROCESS FOR THE TEMPORARY SHAPING OF KERATIN FIBRES

The present invention is directed to the use of at least one guar gum as the sole shape-retention and/or shaping agent in cosmetic compositions intended for a temporary shaping of keratin fibres, and a method for the temporary shaping and/or deformation of these fibres, in particular in the shape of a hairsetting, using this compound.

It is known that the term "hairsetting" in the field of hairdressing denotes the simple operation which consists in giving the hair a non-definitive and temporary shape, generally a wavy shape, such as gentle curls, tight curls and the like, which disappears immediately once the hair is again made wet, in particular when it is washed with water or with shampoo. This is in contrast to a so-called permanent deformation operation, during which genuine chemical transformations and/or treatments (reduction/oxidation) must be performed on the keratin fibres, the final shape in which the hair is set being no longer at all, or only very slightly, sensitive to the above-mentioned external agents in this case.

The most common technique for achieving a hairsetting, or temporary deformation, of the hair consists in first placing hair, which has been wet beforehand or which is still damp, under tension with conventional supports of the curler or roller type and the like, then drying the hair thus placed under tension under a hairstyling hood heated to a temperature ranging from 30° C. to 60° C. for a period of time which may range from 20 to 60 minutes depending on the mass of hair to be dried, then in removing the means for placing the hair under tension used above from the hair thus dried, and finally, in giving a finishing comb through in order to obtain the hair style with the final shape desired. It is also possible to perform a brushing, which consists in shaping the hair using a brush, while the hair is being dried.

The main drawback associated with these techniques is that they always require the use of holding equipment, i.e., rollers, brushes, grips and the like, while the hair is being dried because while the hair is not dry, it cannot keep itself in the desired shape. On the other hand, these techniques nevertheless have the advantage that the hair keeps a natural and pleasant feel.

In order to shape the hair without holding equipment, it has already been proposed to use compositions in the form of a gel which are generally based on crosslinked acrylic polymers. However, these compositions have the drawback of leaving an undesirable deposit on the hair, which is detrimental to the cosmetic properties of the hair; thus, after this operation, the hair has little sheen and feels coarse and sticky.

An object of the present invention is in particular to solve the above discussed problems.

Even more precisely, an object of the present invention is to provide a process for the temporary shaping of keratin fibres which, while making it possible to do away with the use of the usual holding equipment, is nevertheless capable of giving, after the operation, keratin fibres which are of neutral visual appearance and feel.

Following considerable research conducted in this matter, it has now been found, entirely surprisingly and unexpectedly, that this object and others could be achieved by using, in a cosmetically acceptable vehicle, at least one guar gum which is present in the vehicle as the sole shaping and/or shape-retention agent for the keratin fibres. This discovery forms the basis of the current invention.

A subject of the present invention is thus the use, in cosmetic compositions intended for a temporary shaping of keratin fibres, of a guar gum as the sole shaping and/or shape-retention agent for the keratin fibres, in particular the hair, the eyelashes or the eyebrows.

More particularly, a subject of the present invention is thus a method for the temporary shaping and/or deformation of keratin fibres, in particular, the hair, the eyelashes, or the eyebrows, which comprises: (i) formulating a cosmetic composition comprising at least one guar gum for the purpose of shaping and/or retaining the shape of the keratin fibres; and (ii) applying the cosmetic composition to the keratin fibres.

Another subject of the present invention is a method for the temporary shaping and/or deformation of keratin fibres, which comprises the following steps: (i) applying to wet or dry keratin fibres, in particular the hair, a cosmetic composition comprising at least one guar gum as the sole shaping and/or shape-retention agent; wherein the at least one guar gum is present in a cosmetically acceptable vehicle which is preferably an aqueous or aqueous-alcoholic vehicle; (ii) shaping the keratin fibres to which the cosmetic composition has been applied, using a comb, a brush, or the fingers; and (iii) allowing the shaped keratin fibres to dry.

Optionally, the keratin fibres can be styled with a comb, a brush or with the hands following the drying of the fibres.

The guar gums which may be used according to the invention may preferably be chosen from nonionic, anionic and cationic guar gums and mixtures thereof. Nonionic or anionic guar gums are more preferably used.

According to the invention, unmodified or chemically modified nonionic guar gums may preferably be used.

The unmodified nonionic guar gums are, for example, products sold under the name VIDOGUM GH 175 by the company UNIPECTINE and under the name JAGUAR C by the company MEYHALL.

The modified nonionic guar gums which may be used according to the invention are preferably modified by $C_1$–$C_6$ hydroxyalkyl groups.

Among the preferred hydroxyalkyl groups which may be mentioned are hydroxymethyl, hydroxyethyl, hydroxypropyl and hydroxybutyl groups.

These nonionic guar gums are well-known in the state of the art and may, for example, be prepared by reacting corresponding alkene oxides, for example such as propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.2 to 1.2, and more preferably ranges from 0.4 to 1.2.

Such nonionic guar gums optionally modified with hydroxyalkyl groups are, for example, sold under the brand names JAGUAR HP8, JAGUAR HP60, JAGUAR HP120, JAGUAR DC 293 and JAGUAR HP 105 by the company Meyhall, or under the name GALACTASOL 4H4FD2 by the company Aqualon.

The nonionic guar gums may also preferably be modified with $C_1$–$C_6$ hydroxyalkyl or alkyl groups and with fatty chains having from 8 to 30 carbon atoms such as linear or branched alkyl or alkenyl groups. As is known by those skilled in the art, fatty chains which may be used in accordance with the present invention include derivatives of fatty acids, fatty alcohols, and fatty amines.

Such compounds are, for example, described in Patent Applications EP 0,323,623 (U.S. Pat. No. 4,960,876) and EP 0,281,360, the disclosures of which are incorporated herein by reference.

The anionic guar gums which may preferably be used according to the invention may be modified with anionic groups such as carboxylic or phosphate groups and preferably with carboxymethyl groups.

In addition to the anionic groups, the guar gums may possess $C_1$–$C_6$ hydroxyalkyl groups. Among the preferred hydroxyalkyl groups which may be mentioned are hydroxymethyl, hydroxyethyl, hydroxypropyl and hydroxybutyl groups.

Such anionic guar gums optionally modified with hydroxyalkyl groups are, for example, sold under the brand names GALACTASOL 60 H 3 FD and CARBOXYMETHYL GUAR by the company Aqualon.

The cationic guar gums which may preferably be used according to the invention are guar gums containing trialkylammonium cationic groups. In numerical terms, preferably 2 to 30%, and even more preferably 5 to 20%, of the hydroxyl functions of these guar gums bear trialkylammonium cationic groups. Among these trialkylammonium groups, trimethylammonium and triethylammonium groups may preferably be mentioned. Even more preferably, these groups represent from 5 to 20% by weight relative to the total weight of the modified guar gum.

According to the invention, a guar gum modified with 2,3-epoxypropyltrimethylammonium chloride is preferably used.

In addition to the cationic groups, the cationic guar gums may preferably comprise $C_1$–$C_6$ hydroxyalkyl groups. Among the preferred hydroxyalkyl groups which may be mentioned are hydroxymethyl, hydroxyethyl, hydroxypropyl and hydroxybutyl groups.

These guar gums modified with cationic groups are products that are already known per se and are described, for example, in U.S. Pat. Nos. 3,589,578 and 4,0131,307, the disclosures of which are incorporated herein by reference. Such products are moreover sold in particular under the brand names JAGUAR C13 S, JAGUAR C 15 and JAGUAR C 17 by the company Meyhall.

Preferably, a nonionic guar gum is used and, among these nonionic guar gums, more preferably the guar gums modified with hydroxyalkyl groups are used.

The guar gum is present in the cosmetic composition in an amount preferably ranging from 0.2 to 5% by weight relative to the total weight of the composition, and more preferably ranges from 0.6 to 2% by weight.

The cosmetically acceptable vehicle preferably contains water and/or a mixture of water and cosmetically acceptable solvents which are preferably chosen from lower alcohols such as ethanol or isopropanol.

The solvents may be present in concentrations preferably ranging from 0 to 50% by weight relative to the total weight of the composition.

The pH of the compositions used according to the invention preferably ranges from 2 to 12.

Finally, the composition may additionally contain common additives chosen from preserving agents, pH regulators and fragrances. Obviously, a person skilled in the art will exercise care in selecting the optional additives such that the shape-retention properties of the composition are not adversely affected, or are substantially not adversely affected, by these additives.

A composition in accordance with the invention is preferably of non-foaming type.

The compositions used according to the invention are, for example, compositions for fixing and/or styling the hair, or make-up compositions for the eyelashes or the eyebrows, such as mascaras.

Concrete examples illustrating the invention will now be given, but without any limiting nature.

EXAMPLE 1

A gel (1), in accordance with the invention, of the following composition was prepared:

| | |
|---|---|
| Nonionic guar gum modified with hydroxypropyl groups, sold under the brand name JAGUAR HP60 by the company Meyhall | 1.7 g |
| Water q.s | 100 g |

A comparative gel (2) of the following composition was prepared:

| | |
|---|---|
| Crosslinked acrylic acid polymer sold under the brand name CARBOPOL 934 by the company Goodrich | 1.7 g |
| Monoethanolamine q.s. | pH 7 |
| Demineralized water q.s. | 100 g |

10 g of the gel (1) was applied to the left half, and 10 g of the gel (2) to the right half, of a head of washed and drained hair. Curls were formed by rolling the hair up on itself using the fingers, on both sides of the head. The hair was then dried under a hood and, when dry, the hair was combed.

On the left half (invention), the hair was easy to disentangle and the style had body. The hair was soft and shiny.

In contrast, on the right half (comparative), the hair was difficult to disentangle, was coarse and lacked sheen.

EXAMPLE 2

Another gel, in accordance with the invention, of the following composition was prepared:

| | |
|---|---|
| JAGUAR HP 60 | 1.7 g |
| Ethanol | 20 g |
| Demineralized water q.s. | 100 g |

4 g of this gel were applied to the roots of the hair. Hair was shaped using a comb, then was dried under a hood. A controlled head of hair was obtained.

The same cosmetic properties as in Example 1 were obtained with this composition.

EXAMPLE 3

Another gel, in accordance with the invention, of the following composition was prepared:

| | |
|---|---|
| JAGUAR HP 120 | 1 g |
| Ethanol | 20 g |
| Demineralized water q.s. | 100 g |

This gel was applied to the hair. The hair was shaped using a comb or the fingers, then was dried with a hairdryer. A bouffant head of hair with a very natural feel was obtained.

The same cosmetic properties as in Example 1 were obtained with this composition.

EXAMPLE 4

A gel (1), in accordance with the invention, of the following composition was prepared:

| | |
|---|---|
| JAGUAR C 13 S | 1.1 g |
| Ethanol | 30 g |
| Monoethanolamine q.s. | pH 8 |
| Demineralized water q.s. | 100 g |

A comparative gel (2) of the following composition was prepared:

| | |
|---|---|
| Crosslinked acrylic polymer (CARBOPOL 934 from Goodrich) | 1.1 g |
| Ethanol | 30 g |
| Monoethanolamine q.s. | pH 8 |
| Demineralized water q.s. | 100 g |

10 g of the gel (1) was applied to the left half, and 10 g of the gel (2) to the right half, of a head of washed and drained hair. Curls were formed by rolling the hair up on itself using the fingers, on both sides of the head. The hair was then dried under a hood and, when dry, the hair was combed.

On the left half (invention), the hair was easy to disentangle and the style was bouffant.

In contrast, on the right half (comparative), the hair was difficult to disentangle, was coarse and lacked sheen.

EXAMPLE 5

A gel, in accordance with the invention, of the following composition was prepared:

| | |
|---|---|
| JAGUAR C 13 S | 1.4 g |
| Ethanol | 20 g |
| Citric acid | 0.2 g |
| Demineralized water q.s. | 100 g |

The same results as in Example 1 were obtained with this composition.

EXAMPLE 6

A gel, in accordance with the invention, of the following composition was prepared:

| | |
|---|---|
| Carboxymethyl hydroxypropyl guar (GALACTASOL 60 H 3 FD from Aqualon) | 1.7 g |
| Ethanol | 17.2 g |
| Citric acid q.s. | pH 4 |
| Demineralized water q.s. | 100 g |

The same results as in Example 1 were obtained with this composition.

EXAMPLE 7

A mascara, in accordance with the invention, of the following composition was prepared:

Phase A:

| | |
|---|---|
| Beeswax | 6.9 g |
| Carnauba wax | 4.16 g |
| Paraffin | 11.4 g |
| Stearic acid | 7.7 g |

Phase B:

| | |
|---|---|
| Black iron oxide | 5.55 g |

Phase C:

| | |
|---|---|
| Triethanolamine | 3.8 g |
| JAGUAR HP 60 | 0.3 g |
| Preserving agents q.s | |
| Demineralized water q.s. | 100 g |

Phase A was melted at 80° C. and phase B was then introduced and was dispersed using a homogenizer for 30 minutes.

Phase C was prepared by introducing the first three components of this phase into water maintained at 75° C.

An emulsion was then produced by mixing phase C into phase A+B.

The mascara composition was applied to the eyelashes. The eyelashes exhibited good hold.

What is claimed is:

1. A method for the temporary shaping of keratin fibres, wherein said keratin fibres are eyelashes or eyebrows, which comprises:

(i) formulating a cosmetic composition, wherein said cosmetic composition contains a shaping or shape retaining agent consisting of at least one anionic or nonionic guar gum; and (ii) applying said cosmetic composition to said keratin fibres.

2. A method for the temporary shaping of keratin fibres, which comprises:

(i) formulating a cosmetic composition, wherein said cosmetic composition is a makeup composition for the eyelashes or eyebrows, and wherein said cosmetic composition contains a shaping or shape retaining agent consisting of at least one anionic or nonionic guar gum; and (ii) applying said cosmetic composition to said keratin fibres.

* * * * *